United States Patent [19]

Bellina

[11] Patent Number: 4,598,311

[45] Date of Patent: Jul. 1, 1986

[54] LASER SURGICAL OPERATING METHOD AND APPARATUS

[76] Inventor: Joseph H. Bellina, 3439 Kabel Dr., New Orleans, La. 70114

[21] Appl. No.: 598,993

[22] Filed: Apr. 11, 1984

[51] Int. Cl.⁴ .............................................. H04N 7/18
[52] U.S. Cl. ..................................... 358/93; 128/395; 128/419 R; 358/86; 358/229
[58] Field of Search ................... 358/93, 108, 86, 229; 128/906, 908, 665, 419 R, 396, 395

[56] References Cited

U.S. PATENT DOCUMENTS

| | | | |
|---|---|---|---|
| 2,675,462 | 4/1954 | Newton | 358/229 |
| 3,623,283 | 11/1971 | Abromauage | 128/906 |
| 3,891,842 | 6/1975 | Strusinski | 358/229 |
| 3,919,475 | 11/1975 | Dukich | 358/229 |
| 4,051,522 | 9/1977 | Healy | 358/86 |
| 4,354,330 | 10/1982 | Schwartz | 128/906 |
| 4,408,228 | 10/1983 | Mahony | 358/167 |
| 4,467,812 | 8/1984 | Stoller | 128/665 |
| 4,491,131 | 1/1985 | Vassiliadis | 128/395 |
| 4,503,854 | 3/1985 | Jako | 128/395 |

OTHER PUBLICATIONS

*RCA Closed Circuit TV Systems,* "Medical Applications", Book 1, pp. 194–197; Book 11, pp. 89–91, Camden, 1960.

*Primary Examiner*—Howard W. Britton
*Attorney, Agent, or Firm*—Pravel, Gambrell, Hewitt & Kimball

[57] ABSTRACT

A system for microsurgical operation using lasers provides a laser microscope having a housing which carries optical means for viewing an operative field producing an image which is enlarged by the microscope and laser means for selectively concentrating a laser beam on the operative field. Multiple operating room video cameras each generate a video signal and allow simultaneous or selective viewing of the enlarged operative field or a normal operative field so that surgical assistants can view the entire operative procedure while the laser surgeon is operating in either the enlarged or normal field image. One or more video monitors are interfaced with the multiple cameras for selectively displaying either the normal or enlarged image of the operative field.

10 Claims, 6 Drawing Figures

FIG. I.

LASER SURGICAL OPERATING METHOD AND APPARATUS

BACKGROUND OF THE PRESENT INVENTION

1. Technical Field

The present invention relates to a method and apparatus for laser microsurgery, and more particularly relates to a system of microlaser surgery having improved audio-visual support and improved configuration over prior systems and designs.

2. General Background

Laser surgery incorporates the use of a laser and usually a microscope. These devices can be combined into a single unit having a laser microscope "head" which is manipulated by the surgeon. The surgeon uses a micro-manipulator that moves a mirror so as to deflect the laser beam in a desired position upon an operative field. The surgeon views the operative field through a microscope having a pair of spaced apart oculars or a "binocular".

Laser surgery necessarily requires an expanse of equipment and components which can clutter the operating room floor. Not only must the laser itself be supported by a stand having multiple linkage members, but the laser additionally requires a large number of component parts which support and produce the energy for generating the laser beam.

Because the surgeon views the operation through the oculars of the microscope, the magnified image is not always available for viewing by his assistant. This creates a basic problem of communication and logistics between the surgeon and his various operating room technicians. For example, the surgeon must request instruments and thus be delayed for several minutes during an operation. The nurse must prepare various instruments, sutures, and other such operating room equipment which would be normally prepared by the surgical nurse in anticipation of the doctor's requests. In normal operating procedures, the operating room nurse can view the operative field with her normal vision. He or she can quickly anticipate the next instrument or next instruction of the doctor and have it ready. With experienced surgical technicians, these supportive steps are usually done without need of the surgeons' verbal request.

A problem exists in laser microsurgery in that the operating room nurse cannot always anticipate the surgeon's requests because she is unable to see exactly what the surgeon is doing.

Another problem with laser microsurgical procedures is the maintaining of accurate records of the operation for future use. Many laser surgical operative procedures can require additional surgeries at future dates or future supplemental procedures. If a surgeon had a record of each and every step of such a procedure, a subsequent operations would have a high degree of success because of the surgeon's increased education and awareness of his patient by viewing the past record of the operation. Such records could function as a valuable teaching aid. The following list includes several devices that have been patented relating to microsurgical laser systems.

| U.S. Pat. No. | Title | Patentee |
|---|---|---|
| 3,750,670 | "Laser Cauterizer" | Palanos |
| 3,769,963 | "Instrument for Performing Laser Microsurgery and Diagnostic Transalumination of Living Human Tissue" | Goldman |
| 3,783,874 | "Method and Apparatus for Effecting Photo Coagulation" | Koester |
| 3,796,220 | "Stero Laser Endoscope" | Bredemeier |
| 3,910,276 | "Microsurgical Laser System" | Polanyi, et al. |
| 3,348,547 | "Photocoagulating Apparatus" | Kavanaugh, et al. |
| 3,417,754 | "Ophthalmoscopes" | Smat |
| 3,659,613 | "Laser Accessory for Surgical Application" | Bredemeier |
| 3,703,176 | "Slit Lamp Photocoagulator" | Vassiliadis |
| 3,642,007 | "Continuous Wave Laser Surgical Device" | Roberts, et al. |

GENERAL DISCUSSION OF THE PRESENT INVENTION

The present invention provides a microlaser surgical system that includes multiple television cameras (and associated monitors) for viewing the micro-operative field, gross or normal views of the operation, and closeup or endoscopic views. The television cameras are provided in the operating room and form an audio and visual link with a closed circuit television system (CCTV) placed in a remote location from the operating room, the CCTV system manned by a technician. In the closed circuit television remote location, multiple recorders for medical records, patient copies, and doctor copies are made.

A closed loop allows family members to view the operation through a visual and audio link with the operating room. Television cameras in the family viewing room allow the surgeon to converse with the family during the operation but allows the surgeon to close the circuit with a kill switch which breaks the video and audio link with the family viewing room if the surgeon so desires.

The closed circuit television system manned by the technician includes a character generator for adding patient information to the video record of the operating room such as patient name and address, time and date information, hospital number, and identification of operating room personnel, doctors, etc., which accompany the operation, and if desired patient billing information. A central processing unit having a controller and a ram storage can be utilized to receive information from the digital video and audio signal and for receiving information from a patient data file for generating, within given time periods, patient billings, medical visual records, pre-operative care infomation, post-operative care information, miscellaneous patient data, etc. Also interfaced with the central processing unit and ram storage is an in-service medical and nursing file which can provide patient information of that nature.

The closed circuit television system includes monitors disposed within the operating room as well as a monitor disposed in the remote family viewing room, as well as multiple monitors in a remote location manned by a technician. The multiple cameras in the operating room are used for the purpose of displaying: (a) the microscopic field of view as seen by the surgeon, and (b) an overview of the operating room including the patient, the surgeon, assisting surgeons, operating room technicians, and the anesthesiologist. Closeup views of the operation showing a normal rather than microscopic operative field can also be displayed in the operating room television monitors. These multiple monitors allow all personnel assisting with the operation including the anesthesiologist, the operating room technicians and assisting surgeons to view all aspects of the operation as it occurs. At the same time, the closed circuit television technician monitors and records the camera-generated video signals for a permanent record of all phases of the operation. Thus, the closed circuit television technician would be viewing as many as four monitors including: (1) a gross view, (2) a microscopic view, (3) an overview of the operating room, and (4) a closeup or endoscopic view for viewing the localized operating area but in a normal field.

A component support includes a telescoping cylinder which is supported above the operating room ceiling by structural beams, concrete, or other such structural portions of the building in which the operating room is housed. The hydraulic cylinder includes a cylinder and an extending rod which supports a pedestal having an internal space. Supply cables such as electrical power cables are routed to the internal space from the top side of the pedestal. The lowermost portion of the pedestal provides an expansive horizontal work surface upon which numerous components can be stored which support operation of the laser. This would include, for example, light sources and a strobe for still photographs as well as electronic support for the laser itself. The pedestal would provide an outer terminal plate having a plurality of electrical outlets into which the various components could be removably connected.

The pedestal would additionally provide multiple openings through which television cables, audio cables and the like could be passed. Thus the entire support apparatus including multiple cables, electrical support and other power supply would come from above the operating field and would not in any way restrict 360° degree travel about the operating room table.

In the preferred embodiment, the hydraulic cylinder would retract the entire pedestal into a position above the operating room ceiling so that the lowermost, horizontal working surface is flush with the ceiling. Thus the ceiling would provide an opening through which the lowermost work surface could be withdrawn. Alternatively, the opening would be large enough for the passage of the pedestal and all of the components with the lowermost work surface registering with and contacting the ceiling when the device is in the fully withdrawn position. Thus, the withdrawn apparatus would be completely removed from view after an operation were completed so that a surgeon could go from operation to operation without fear that the various controls, digital settings, switches, etc., had not been tampered with between operating procedures such as by cleaning or janitorial services, for example.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

Figure 1:
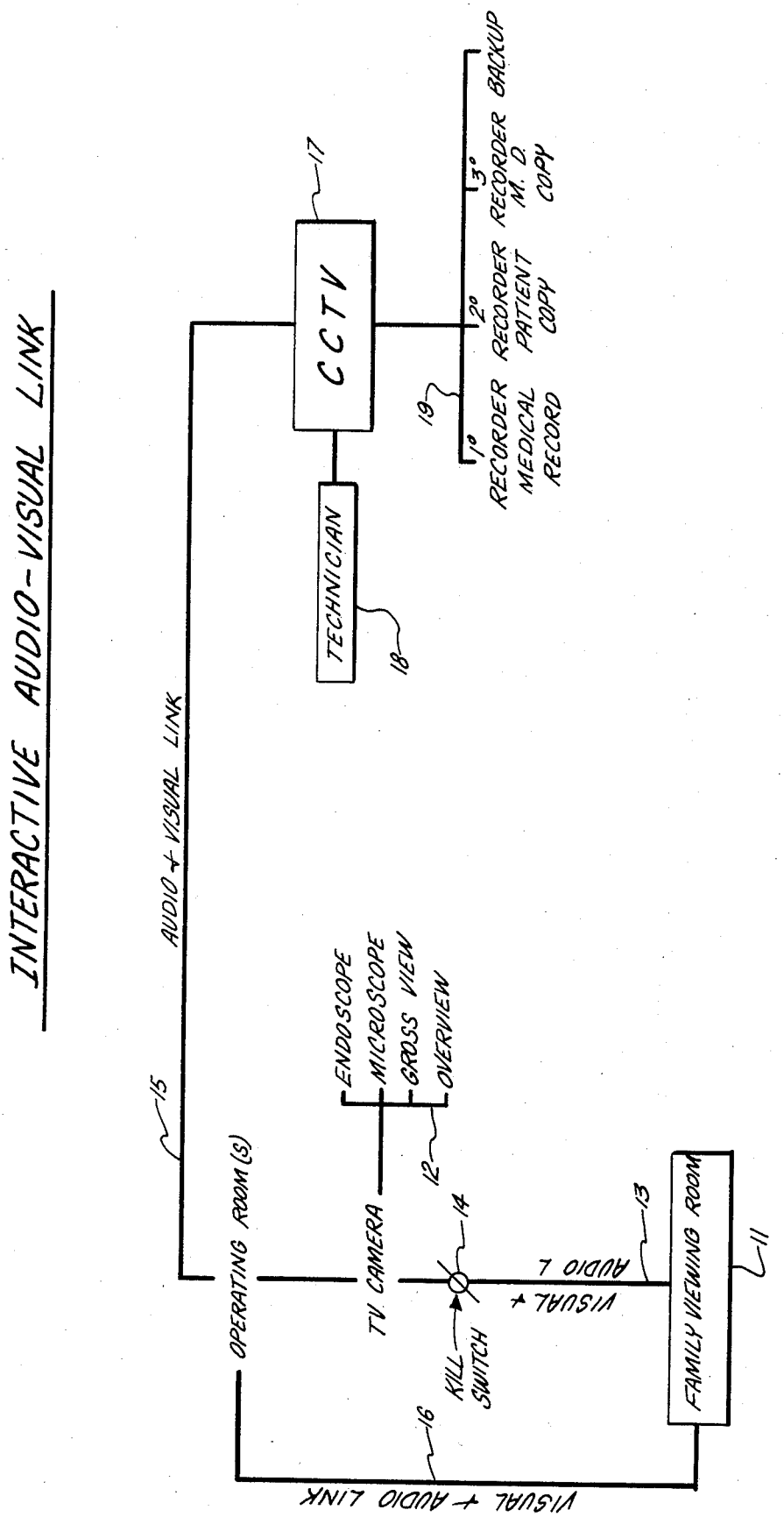
FIG. 1 is a schematic view of the preferred embodiment of the apparatus of the present invention illustrating the interactive audio visual link portion thereof which includes the CCTV and family viewing loop.

FIGS. 1-4 provide schematic illustrations of the preferred embodiment of the apparatus of the present invention. In FIG. 1 there can be seen an overview of the interactive audio-visual link schematically illustrating the closed circuit television (CCTV) loop and family viewing loop. The CCTV loop includes multiple television cameras 12 including endoscopic, microscopic, gross view and overview television cameras which are used in the operating room during microsurgery. An audio-visual link 13 cooperates with kill switch 14 to supply to a family viewing room 15 an audio-visual image of the operation. The audio-visual link is provided to the family viewing room through lines 15, 16 after the generated signal is received by a closed circuit television remote location 17 manned by a technician 18. Multiple recorders 19 record the operation including multiple copies for medical and hospital records, patient copies, and physician copies.

Figure 2:
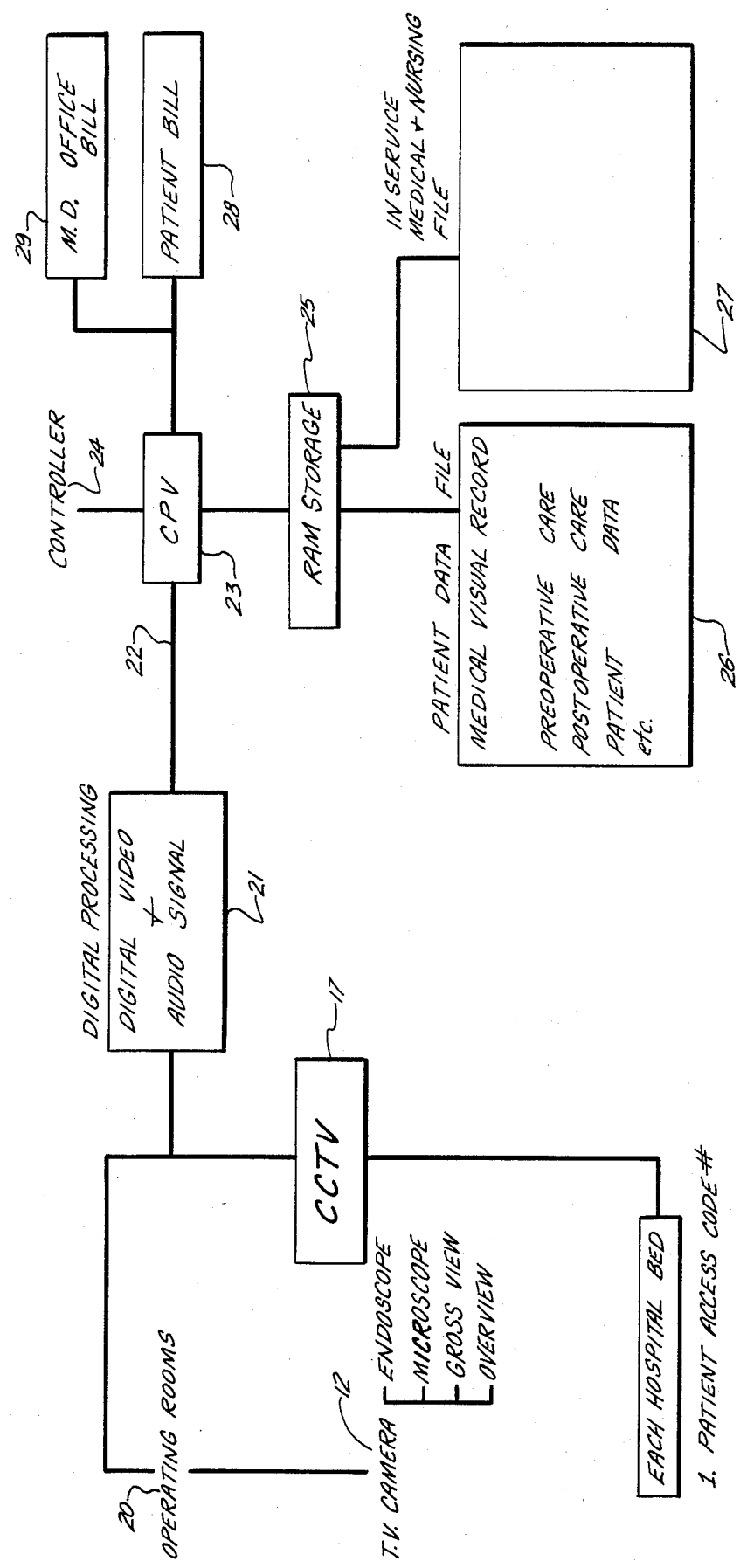
FIG. 2 is an overall schematic view of the preferred embodiment of the apparatus of the present invention illustrating the interactive audio visual link.

In FIG. 2, the closed circuit television remote location 17 is shown cooperating with the various television cameras 12 of the operating room 20. Digital processing equipment 21 provides information through lines 22 to central processing unit 23 having a controller 24. Ram storage 25 provides patient information through a patient data file 26 including such information as pre-operative and post-operative care, medical visual records, and miscellaneous patient data. Ram storage 25 is also provided with in-service medical and nursing information 27. All the videotape signals are digitalized and stored in the computer. Thus all storage is in the computer and instead of soft copies the computer stored information affords instant access. Otherwise a clerk would have to go to a patient library, search for a particular tape and look for the pertinent viodeotape information. With the present system, an access code is used to obtain the desired videotape information. Thus CPU 23 can access RAM 25 and be used to prepare eg., a patient billing 28 and M.D. office bill 29.

Figure 3:
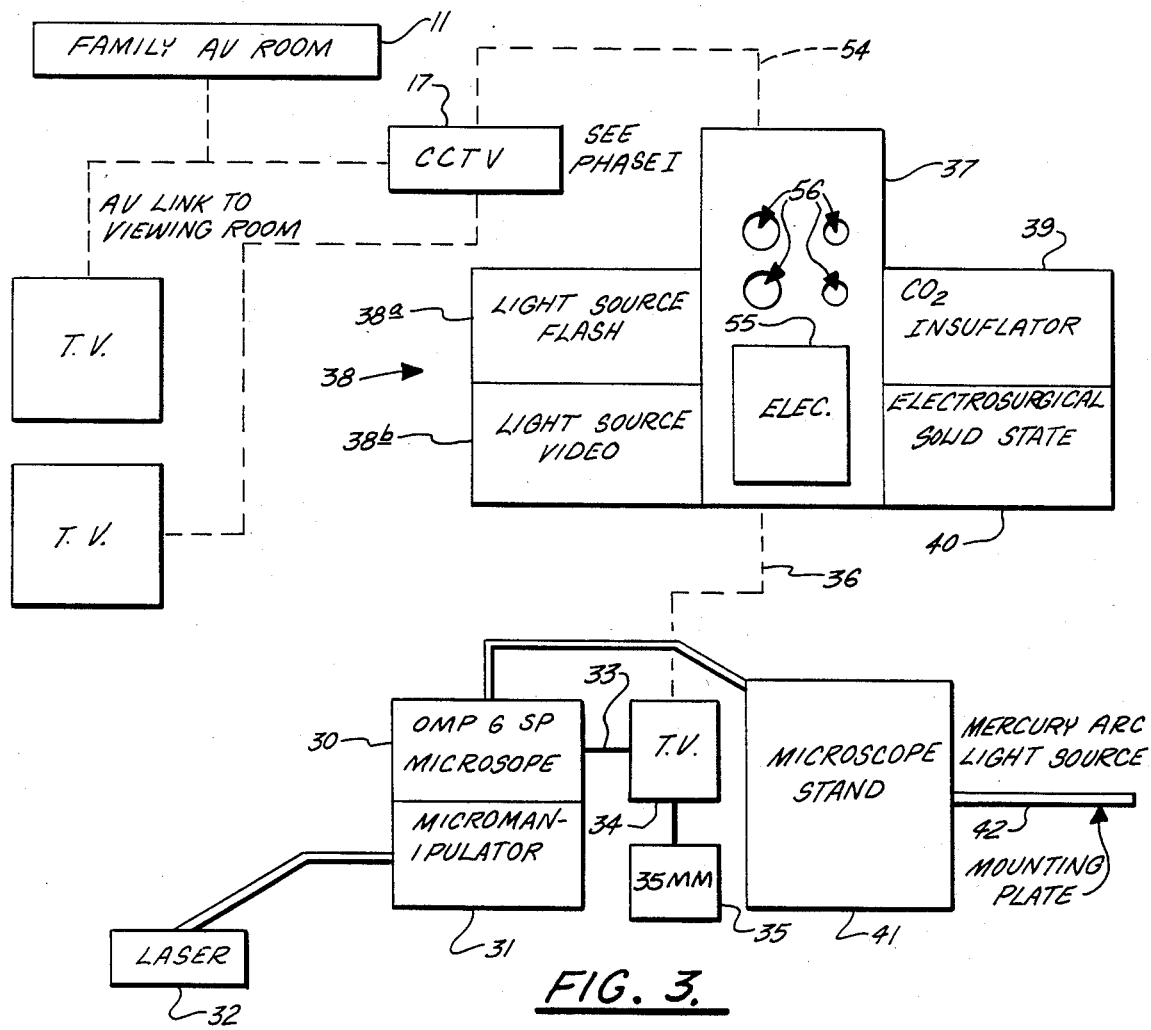
FIG. 3 is a schematic illustration of the laser microscope, its supportive components, and its interface with the CCTV system.

FIG. 3 illustrates the operating room schematic layout of the laser microscope 30. Laser microscope 30 includes a micro-manipulator 31 which is used to manipulate laser 32 so that a laser beam of desired intensity and size is focused on the operative location. The microscope incorporates beam splitter 33 so that television camera 34 and still camera 35 are interfaced with the objective of the microscope so that a video record as well as a still photograph record can be made of the entire operative procedure. Cable 36 links television camera 34 with pedestal 37 (see FIGS. 5 and 6) that supports a plurality of components including light source 38, light source 39, and CO₂ laser support components 40.

Microscope 30 is supported by microscope stand 41 which could be, for example, a Contravis-type microscope stand. Mercury or light source supported by a mounting plate 42 completes the laser microscope of FIG. 3.

Figure 4:
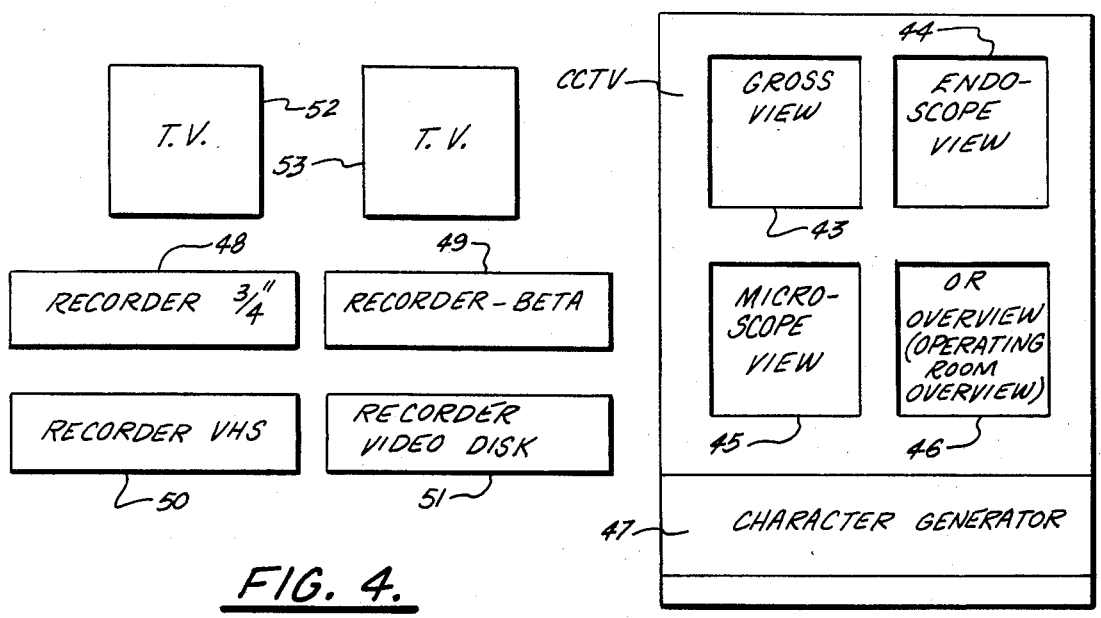
FIG. 4 is a schematic illustration of the closed circuit television remote base.

FIG. 4 schematically illustrates the closed circuit television 17 including small multiple monitor displays 43–46 including a gross view, endoscopic view, microscopic view and overview of operating room. Monitors 52, 53 can be full size color monitors which allow technician 18 to adjust the picture quality (i.e., light control, brightness, hue, color, etc.) being recorded on video recorders 48–51.

The character generator 47 is used for the input of patient data information eg., the patient's name, their hospital number, the date of a particular operation, the planned procedure that was expected before operation, the actual procedure that was done, etc. The character generator is interfaced with computer 23 so that name and all related data and documents can be routed first to a filing system, a billing service, etc. The character generator 47 labels the videotape so that a later reviewer can identify the material and the generator 47 identifies desired material when taping so that you can go back and pull that material later. For example, if a surgeon is operating on a particular ovarian disease, the technician 18 marks that tape in places according to the surgeon's instruction. The computer can later be asked to access all ovarian surgeries with the previous common character marks.

Multiple records 48–52 are used to make patient copies, hospital copies and physician copies of the operation as recorded by the cameras. The family viewing room 15 is also indicated in FIG. 3 as connected to the closed circuit television remote location 17. Cable 54 joins component pedestal 37 with closed circuit television remote location 17 providing video information from the various operating room cameras as above-described.

Exemplary components are light sources 38 (including still camera flash 38a and TV camera light source 38b), carbon dioxide insufflator 39, and electrosurgical solid state unit 40. Pedestal 37 includes electrical panel 55 having a plurality of terminals to which the various components 38–40 can be plugged in for receiving electric power. Pedestal 37 can also have multiple apertures 56 through which television cables, audio cables and the like can pass into the interior space of pedestal 37.

Figure 6:
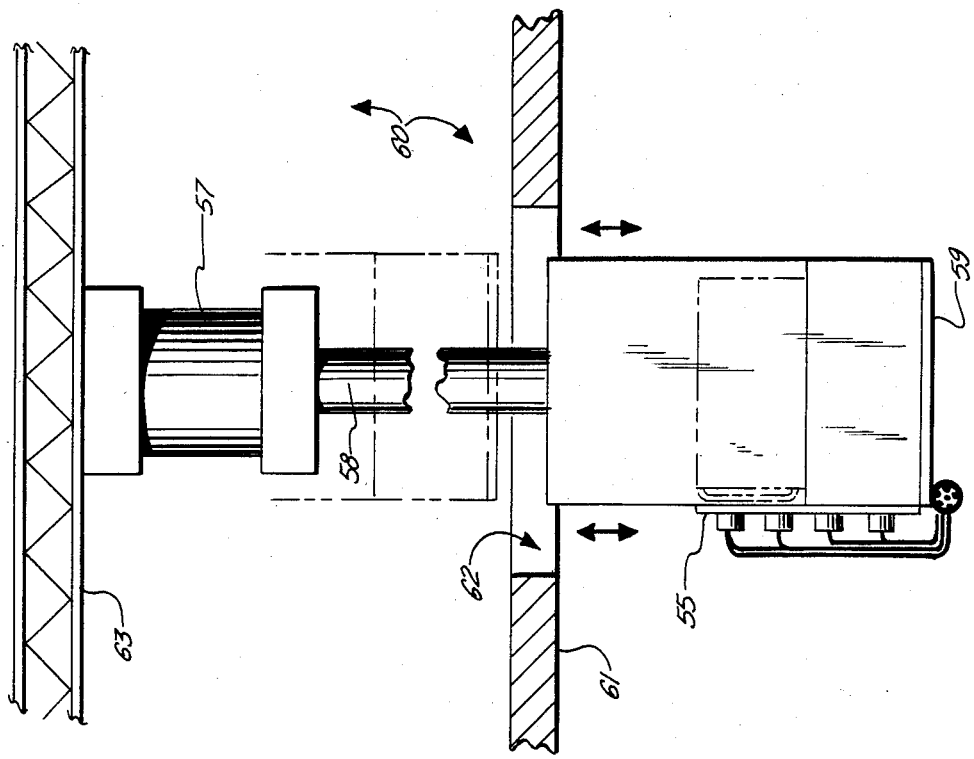
FIG. 6 is a side view of the laser microscope component support platform of FIG. 5.
Figure 5:
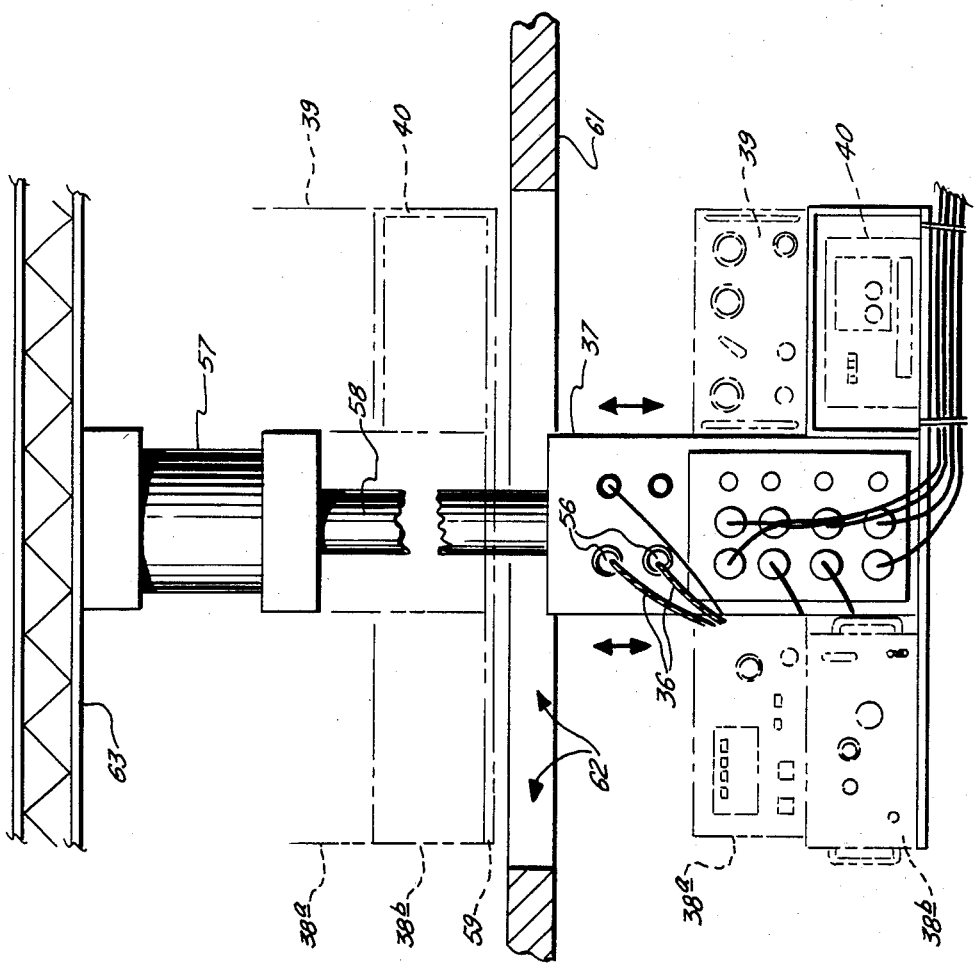
FIG. 5 is a front sectional view of the preferred embodiment of the apparatus of the present invention illustrating the laser microscope component support platform.

FIGS. 5 and 6 best show pedestal 37 as comprising a hydraulic cylinder 57 which actuates a piston rod 58 so that the rod can be expanded or contracted in order to raise or lower working surface 59 which supports a plurality of components 38–40. Apertures 56 allow cables 36 from one or more of the television cameras to be routed into the area 60 above ceiling 61. An opening 62 in ceiling 61 allows surface 59 and its contained components 38–40 to be withdrawn into the area 60 above ceiling 61 as shown by the phantom lines of FIGS. 5 and 6. Hydraulic cylinder 57 could be attached to any structural beam such as beam 63 of FIGS. 5 and 6. Alternatively, cylinder 57 could attach directly to the concrete slab above ceiling 61 or any other suitable structural portion of the building which could support at least several hundred pounds of weight.

Because many varying and different embodiments may be made within the scope of the inventive concept herein taught, and because many modifications may be made in the embodiments herein detailed in accordance with the descriptive requirement of the law, it is to be understood that the details herein taught are to be interpreted as illustrative and not in a limiting sense.

What is claimed as the invention is:

1. A system for microsurgical operation using lasers comprising:
   a. A laser microscope system having a housing which carries optical means for viewing an operative field image which is enlarged by the microscope and laser means for selectively concentrating a laser beam on the operative field;
   b. multiple operating room video cameras each generating a video signal and allowing simultaneous or selective viewing of the enlarged operative field image or of a normal operative field, or of a gross view of the operating room area so that surgical assistants selected and persons not in the operating room can view the operative procedure while the laser surgeon is operating, in either the enlarged or normal field image; and
   c. one or more video monitors interfaced with the multiple cameras for selectively displaying either the normal or enlarged images of the operative field in the operating room and in remote locations.

2. The laser surgical system of claim 1 further comprising one or more closed circuit television loops communicating with a remote location which includes:
   a. a video camera recording an image of the remote location;
   b. a monitor at the remote location which displays at least one of the operating room video camera signals; and
   c. switch means for terminating the video signal to the remote location monitor.

3. The laser surgical system of claim 1, wherein the remote location communicates with the operating room via a loop forming an audio and visual link.

4. The laser surgical system of claim 1, wherein the laser microscope includes a floor mounted adjustable stand positioned under the elevated surface means so that components supporting operation of the laser microscope can be connected thereto from a position above the laser microscope.

5. The laser surgical system of claim 1 further comprising recorder means for recording each video camera signal.

6. The laser surgical system of claim 5 further comprising character generator means for adding patient information to one or more of the video signals.

7. The laser surgical system of claim 1 further comprising elevated surface means suspended above the operative field for carrying one or more components of the laser microscope which activate the laser microscope and are separate components from the microscope optics viewed by the surgeon.

8. The laser surgical system of claim 7, wherein the elevated surface means comprises:
   a. a generally vertical pedestal extendable and retractable with respect to the ceiling area of an operating room in which the laser surgical operative procedure is to be performed;
   b. horizontal surface means radiating from the pedestal for providing an expansive surface upon which separate electrical components can be placed;
   c. electrical supply means for supplying electrical power to the pedestal;

d. electrical terminal means on the surface of the pedestal and connected to the electrical supply means for supplying electrical power connections for the components;
e. an internal pedestal space; and
f. one or more apertures in the pedestal wall and communicating with the internal pedestal space so that component cables can travel from the expansive work surface to the internal pedestal space.

9. The laser surgical system of claim 8, wherein the pedestal includes a telescoping arm which can retract the expanded surface to a position generally coplanar the ceiling of an operating room in which the surface is disposed.

10. The laser surgical system of claim 9, wherein the expanded surface is a generally flat horizontal surface mounted at generally right angles to the lower end portion of the pedestal.

* * * * *